United States Patent [19]
Toth et al.

[11] Patent Number: 5,506,115
[45] Date of Patent: Apr. 9, 1996

[54] REAGENT AND METHOD FOR DETERMINING ACTIVITY OF HERPES PROTEASE

[75] Inventors: Mihaly V. Toth, St. Louis; Arthur J. Wittwer, Ellisville; Barry C. Holwerda, Richmond Heights, all of Mo.

[73] Assignee: G. D. Searle & Co., Chicago, Ill.

[21] Appl. No.: 235,412

[22] Filed: Apr. 29, 1994

[51] Int. Cl.$^6$ .............................. C07K 5/00; C07K 7/00; C07K 17/00; C12Q 1/37
[52] U.S. Cl. .................... 435/23; 435/24; 435/5; 530/326; 530/327; 530/328; 530/329; 530/330
[58] Field of Search ................. 530/326–330; 435/23, 24, 5

[56] References Cited

U.S. PATENT DOCUMENTS 5,011,910  4/1991  Marshall et al. ................. 530/329

FOREIGN PATENT DOCUMENTS 514830  11/1992  European Pat. Off. .
01291   1/1993   WIPO .

OTHER PUBLICATIONS

Ljungman et al., *J. Infect. Dis.*, 162, 244 (1990).
Gately et al, *J. infect. Dis.*, 161, 711 (1990).
Lui and Roizman, *J. Virol.*, 65, 5149 (1991).
A. R. Welch et al., *Proc. Natl. Acad. Sci USA*, 88, 10792 (1991).
G. Guilbault, *Enzymatic Methods of Analysis*, 43–47 (1970).
S. Netzel–Arnett et al, *Anal. Biochem.*, 195, 86 (1991).
C. Garcia–Echeverria, *FEBS Lett.*, 297, 100 (1992).
C. Garcia–Echeverria, *Biochem. and Biophys. Res. Comm.*, 187, 615 (1992).
E. Matayoshi et al, *Science*, 247, 954 (1990).
G. Wang et al, *Tet. Lett.*, 31, 6493 (1990).
L. Maggiora et al, *J. Med. Chem*, 35, 3727 (1992).

*Primary Examiner*—Jill Warden
*Assistant Examiner*—Sheela J. Huff
*Attorney, Agent, or Firm*—Joseph W. Bulock; J. Timothy Keane

[57] ABSTRACT

A class of compounds is described for use as fluorogenic substrates for herpesvirus proteases and for use in an assay to identify inhibitors of herpesvirus proteases. Compounds of particular interest are defined by Formula II Z—W—Gly—Val—Val—Asn—Ala—Ser—Ala—Arg—Leu—Ala—Y   (II)

[SEQ ID NO: 33]

wherein W is selected from glycine, 4-aminobutyric acid, 5-aminopentanoic acid, 6-aminocaproic acid and 7-aminoheptanoic acid; wherein Y is selected from EDANS, Abz, DANSYL, nicotinic acid, 4-guanidino-benzoic acid, N-methyl-Abz, 4-chloro-Abz, 5-chloro-Abz, 6-chloro-Abz, 3,5-dibromo-Abz, 6-amino-nicotinic acid, 2-aminonicotinic acid, 2-chloronicotinic acid, niflumic acid and fluorogenic derivatives thereof; and wherein Z is selected from tryptophan, tyrosine, phenylalanine, p-nitrophenylalanine, m-nitrophenylalanine, DABSYL, DABCYL and halogenated derivatives thereof.

11 Claims, 2 Drawing Sheets

Time course of change in fluorescence emission during hydrolysis of peptide (1) by assemblin. The arrow indicates the addition of assemblin to 10 μM substrate (1) in a volume of 2 mL assay buffer. After the addition of the protease, the substrate is immediately cleaved, and the fluorescence emission increases to 10-fold within 30 min.

Time course of change in fluorescence emission during hydrolysis of peptide (1) by assemblin. The arrow indicates the addition of assemblin to 10 μM substrate (1) in a volume of 2 mL assay buffer. After the addition of the protease, the substrate is immediately cleaved, and the fluorescence emission increases to 10-fold within 30 min.

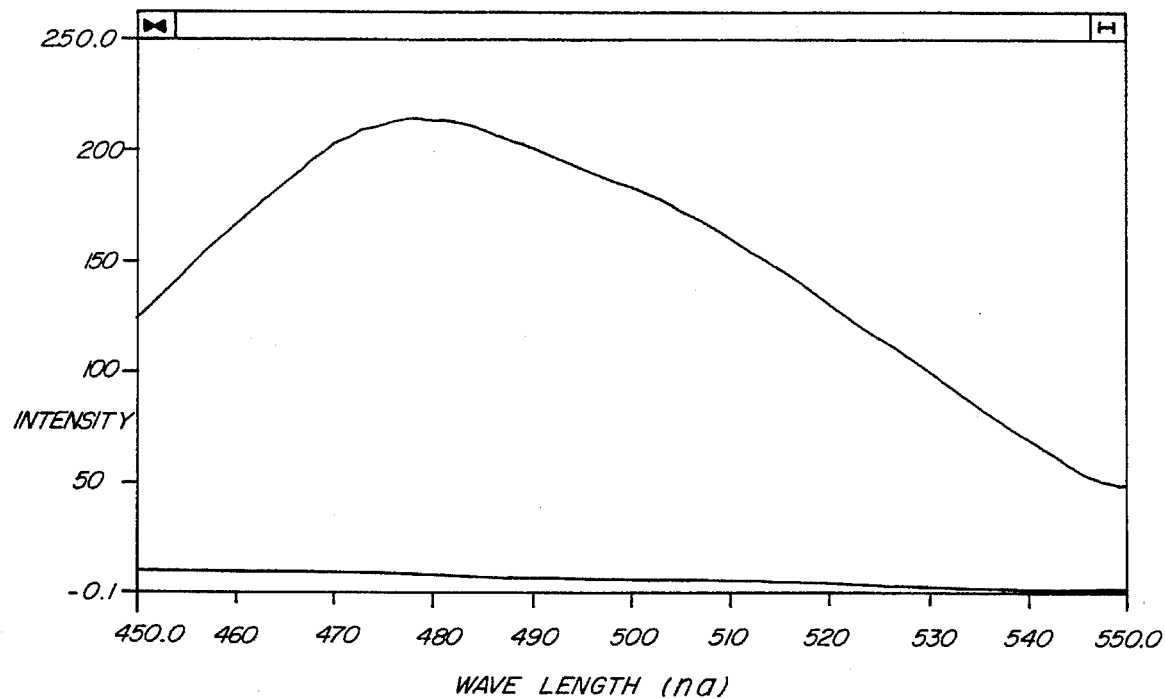

FIG. 2

Fluorescence emission spectra of 2 μM substrate (1) and 2 μM C-terminal cleavage product (SARL-Edans) in assay buffer, showing almost completely quenched fluorescence in substrate (1) due to the proximity of the fluorescence donor (Edans) and quenching acceptor (Dabcyl) chromophores. Fluorescence intensity plotted versus emission wavelength at 340 nm excitation wavelength.

1

REAGENT AND METHOD FOR DETERMINING ACTIVITY OF HERPES PROTEASE

FIELD OF THE INVENTION

This invention relates to reagents and a method for determining the activity of herpesvirus proteases. More particularly, the invention relates to fluorogenic substrates and a fluorometric assay for CMV protease and other herpesvirus proteases.

BACKGROUND OF THE INVENTION

There is a great need for new therapies active in the treatment of viral diseases. Whereas there has been great progress in developing a variety of therapies for the treatment of bacterial infections, there are few viable therapies for the treatment of viruses in general and herpesvirus in particular. Herpesviridae is a family of DNA viruses which include herpes simplex virus type-1 (HSV-1) herpes simplex virus type-2 (HSV-2), cytomegalovirus (CMV), varicella-zoster virus (VZV), Epstein-Barr virus, human herpesvirus-6 (HHV6), human herpesvirus-7 (HHV7), pseudorabies and rhinotracheitis, among others. Ganciclovir, acyclovir and foscarnet are currently utilized for the treatment of herpesvirus infections. However, these therapies can have substantial side effects based on their deleterious effects on host cell DNA replication, or they can be used to treat only a limited number of herpesviruses. In addition, herpesviruses are known to develop resistance to these therapies which causes a progressive decline in efficacy [Ljungman et al., *J. Infect. Dis.*, 162, 244 (1990) and Gately et al, *J. Infect. Dis.*, 161, 711 (1990)].

It is known that herpesviruses express their genetic content by directing the synthesis of a number of proteins encoded by the herpesvirus DNA in the host cell. One of the important virus encoded proteins is made as a precursor consisting of an amino terminal-located protease and carboxyl terminal-located assembly protein. This precursor is proteolytically processed in an autocatalytic manner at a specific amino acid sequence known as the "release" site yielding separate protease and assembly protein. The assembly protein is cleaved further by the protease at another specific amino acid sequence known as the "maturation" cleavage site. Recently, EP No. 514,830, published Nov. 25, 1992, describes a virus-specific serine protease which has a role in herpesvirus replication. Additionally, Lui and Roizman (*J. Virol*, 65, 5149 (1991)) describe the sequence and activity of a protease and the associated assembly protein encoded by $U_L 26$ of HSV-1. A. R. Welch et al (*Proc. Natl. Acad. Sci. USA*, 88, 10792 (1991)) describe the related protease (also known as assemblin) and assembly protein encoded by $U_L 80$ of CMV. An approach currently being investigated for potential use in the treatment of herpesvirus infections is the development of inhibitors of herpesvirus proteases.

Various inhibitors of herpesvirus proteases are described in applicants' copending application.

In order to facilitate the rapid identification of herpesvirus protease inhibitors, an assay which allows for high throughput and linearity is desirable. Initial assays used in the characterization of herpesvirus proteases have been based on electrophoretic separation of products. See EP 514,830. Such method is impractical for screening large numbers of enzymatic inhibitors. An assay which allows for quantitative kinetic characterization of the interaction of the inhibitors with herpesvirus proteases is more preferred.

Resonance energy transfer has been utilized in the biochemical study of hydrolytic enzymes because of the technique's high sensitivity. See e.g. Guilbault, *Enzymatic Methods of Analysis*, 43–47 (1970).

G. Marshall and M. Toth, in U.S. Pat. No. 5,011,910, describe the use of fluorogenic substrates for the determination of HIV proteases. S. Netzell-Arnett et al (*Anal. Biochem.*, 195, 86 (1991)) describe the use of a fluorescent assay for human matrix metalloproteinases.

C. Garcia-Echeverria and D. Rich describe the use of quenched fluorogenic peptide substrates in an investigation of the sensitivity of the cysteine protease, papain, to modifications in the P1' and P2' sites (*FEBS Lett.*, 297, 100 (1992), and *Biochem. and Biophys. Res. Comm.*, 187, 615 (1992)). E. Matayoshi et al describe the use of an EDANS/DABCYL-containing substrate for assaying HIV protease (*Science*, 247, 954 (1990)). G. Wang et al use similar groups on their related substrate (*Tet. Lett.*, 31, 6493 (1990)). L. Maggiora et al describe a solid-phase peptide synthesis method of preparing EDANS/DABCYL-containing substrates (*J. Med. Chem.*, 35, 3727 (1992)).

BRIEF DESCRIPTION OF THE DRAWINGS

FIG. 2 is a graphical representation which shows the time course of change in fluorescence emission spectra during hydrolysis of substrate DE1 [SEQ ID NO:34]by CMV assemblin.

DETAILED DESCRIPTION OF THE INVENTION

Figure 1:
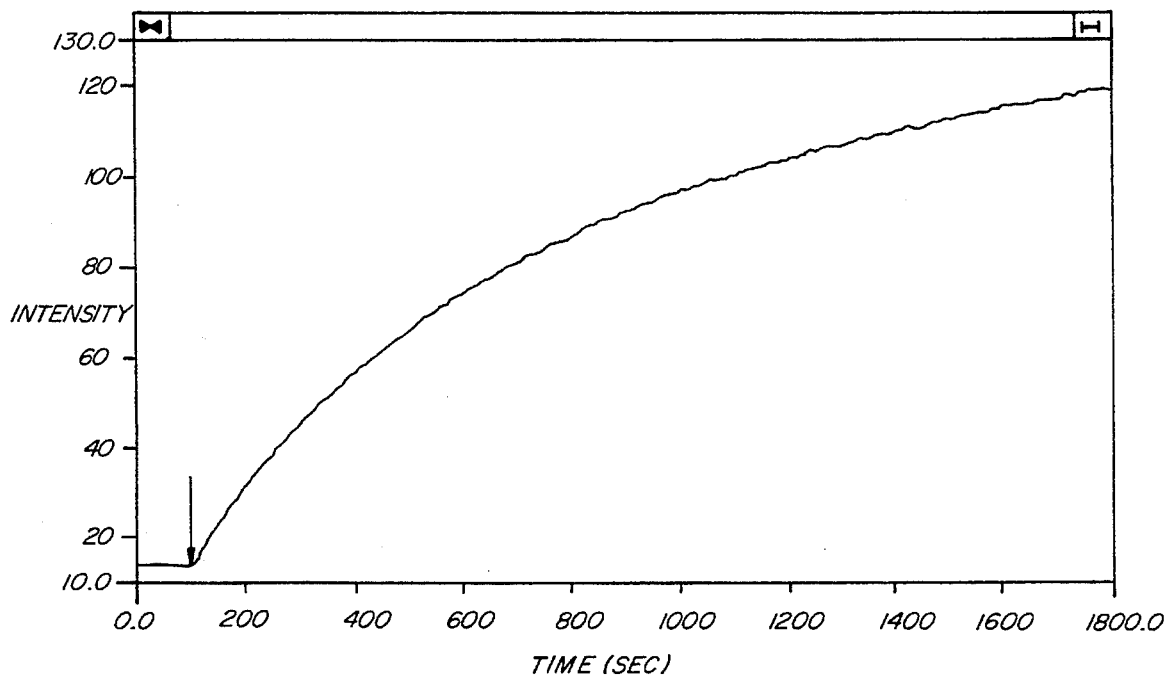
FIG. 1 is a graphical representation which shows the fluorescence emission spectra of 2 μM substrate DE1 [SEQ ID NO:34]and 2 μM Ser-Ala-Arg-Leu-EDANS (the C-terminal cleavage product)[SEQ ID NO:36].

In accordance with the present invention, fluorogenic substrates and a fluorometric assay for herpesvirus protease, and preferably the CMV protease (also known as assemblin) encoded by $U_L 80$, utilizing these substrates are provided.

A class of compounds useful as substrates for herpesvirus proteases is defined by Formula I

$$Z\text{-}(W)_m\text{-}X\text{-}(V)_n\text{-}Y \qquad (I)$$

wherein X is an amino acid sequence sufficient for substrate recognition by a herpesvirus protease; wherein V and W are independently selected from aminoalkylcarboxylic acids; wherein m and n are numbers independently selected from 0 and 1; and wherein one of Y and Z is a fluorogenic donor radical and the other is an acceptor radical.

A preferred class of compounds consists of those compounds of Formula I wherein X is a peptide containing six to sixteen amino acids, inclusive; wherein V and W are independently selected from lower aminoalkylcarboxylic acids; wherein the fluorogenic donor radical is a fluorescence emitting radical; and wherein the acceptor radical is an aromatic radical which absorbs the fluorescence energy of the fluorogenic donor radical when the acceptor radical and the fluorogenic donor radical are covalently held in close proximity.

A more preferred class of compounds consists of those compounds of Formula I, wherein X is selected from -Val-Val-Asn-Ala-Ser-Ala-Arg-Leu- [SEQ ID NO:1], -Gly-Val-Val-Asn-Ala-Ser-Ala-Arg-Leu- [SEQ ID NO:2], -Val-Val- Asn-Ala-Ser-Ala-Arg-Leu-Ala- [SEQ ID NO:3], -Ala-Gly-Val-Val-Asn-Ala-Ser-Ala-Arg-Leu- [SEQ ID NO:4], -Gly-Val-Val-Asn-Ala-Ser-Ala-Arg-Leu-Ala- [SEQ ID NO:5], -Val-Val-Asn-Ala-Ser-Ala-Arg-Leu-Ala-Thr- [SEQ ID NO:6],-Gln-Ala-Gly-Val-Val-Asn-Ala-Ser-Ala-Arg-Leu- [SEQ ID NO:7], -Ala-Gly-Val-Val-Asn-Ala-Ser-Ala-Arg-Leu-Ala- [SEQ ID NO:8], -Gly-Val-Val-Asn-Ala-Ser-Ala-Arg-Leu-Ala-Thr- [SEQ ID NO:9], -Val-Val-Asn-Ala-Ser-Ala-Arg-Leu-Ala-Thr-Ala- [SEQ ID NO:10], -Ala-Gln-Ala-Gly-Val-Val-Asn-Ala-Ser-Ala-Arg-Leu- [SEQ ID NO:11], -Gln-Ala-Gly-Val-Val-Asn-Ala-Ser-Ala-Arg-Leu-Ala- [SEQ ID NO:12], -Ala-Gly-Val-Val-Asn-Ala-Ser-Ala-Arg-Leu-Ala-Thr- [SEQ ID NO:13], -Gly-Val-Val-Asn-Ala-Ser-Ala-Arg-Leu-Ala-Thr-Ala- [SEQ ID NO:14], -Arg-Ala-Gln-Ala-Gly-Val-Val-Asn-Ala-Ser-Ala-Arg-Leu- [SEQ ID NO:15], -Ala-Gln-Ala-Gly-Val-Val-Asn-Ala-Ser-Ala-Arg-Leu-Ala [SEQ ID NO:16], -Gln-Ala-Gly-Val-Val-Asn-Ala-Ser-Ala-Arg-Leu-Ala-Thr- [SEQ ID NO:17], -Ala-Gly-Val-Val-Asn-Ala-Ser-Ala-Arg-Leu-Ala-Thr-Ala- [SEQ ID NO:18], -Glu-Arg-Ala-Gln-Ala-Gly-Val-Val-Asn-Ala-Ser-Ala-Arg-Leu- [SEQ ID NO:19], -Arg-Ala-Gln-Ala-Gly-Val-Val-Asn-Ala-Ser-Ala-Arg-Leu-Ala- [SEQ ID NO:20], -Ala-Gln-Ala-Gly-Val-Val-Asn-Ala-Ser-Ala-Arg-Leu-Ala-Thr- [SEQ ID NO:21], -Gln-Ala-Gly-Val-Val-Asn-Ala-Ser-Ala-Arg-Leu-Ala-Thr-Ala- [SEQ ID NO:22], -Ala-Glu-Arg-Ala-Gln-Ala-Gly-Val-Val-Asn-Ala-Ser-Ala-Arg-Leu- [SEQ ID NO:23], -Glu-Arg-Ala-Gln-Ala-Gly-Val-Val-Asn-Ala-Ser-Ala-Arg-Leu-Ala- [SEQ ID NO:24], -Arg-Ala-Gln-Ala-Gly-Val-Val-Asn-Ala-Ser-Ala-Arg-Leu-Ala-Thr- [SEQ ID NO:25], -Ala-Gln-Ala-Gly-Val-Val-Asn-Ala-Ser-Ala-Arg-Leu-Ala-Thr-Ala- [SEQ ID NO:26], -Val-Ala-Glu-Arg-Ala-Gln-Ala-Gly-Val-Val-Asn-Ala-Ser-Ala-Arg-Leu- [SEQ ID NO:27], -Ala-Glu-Arg-Ala-Gln-Ala-Gly-Val-Val-Asn-Ala-Ser-Ala-Arg-Leu-Ala- [SEQ ID NO:28], -Glu-Arg-Ala-Gln-Ala-Gly-Val-Val-Asn-Ala-Ser-Ala-Arg-Leu-Ala-Thr- [SEQ ID NO:29]and -Arg-Ala-Gln-Ala-Gly-Val-Val-Asn-Ala-Ser-Ala-Arg-Leu-Ala-Thr-Ala- [SEQ ID NO:30]and homologs thereof; wherein V and W are independently selected from glycine, 4-aminobutyric acid, 5-aminopentanoic acid, 6-aminocaproic acid and 7-aminoheptanoic acid; wherein the fluorogenic radical is selected from EDANS, 2-aminobenzoic acid (Abz), 5-dimethylamino-naphthalene-1-sulfonyl (DANSYL), nicotinic acid, 4-guanidino-benzoic acid, N-methyl-Abz, 4-chloro-Abz, 5-chloro-Abz, 6-chloro-Abz, 3,5-dibromo-Abz, 6-amino-nicotinic acid, 2-amino-nicotinic acid, 2-chloronicotinic acid, niflumic acid and fluorogenic derivatives thereof; and wherein the acceptor radical is selected from tryptophan, tyrosine, phenylalanine, p-nitrophenylalanine, m-nitrophenylalanine, DABSYL, DABCYL and halogenated derivatives thereof.

Within Formula I there is a subclass of compounds of high interest represented by Formula II Z—W—Gly—Val—Val—Asn—Ala—Ser—Ala—Arg—Leu—Ala—Y (II)
[SEQ ID NO:31]

wherein W is an aminoalkylcarboxylic acid; wherein one of Y and Z is a fluorogenic radical and the other is an acceptor radical.

A preferred class of compounds consists of those compounds of Formula II wherein W is a lower aminoalkylcarboxylic acid; wherein Y is a fluorogenic radical; and wherein Z is an acceptor radical.

A more preferred class of compounds consists of those compounds of Formula II wherein W is selected from glycine, 4-aminobutyric acid, 5-aminopentanoic acid, 6-aminocaproic acid and 7-aminoheptanoic acid; wherein Y is selected from EDANS, Abz, DANSYL, nicotinic acid, 4-guanidino-benzoic acid, N-methyl-Abz, 4-chloro-Abz, 5-chloro-Abz, 6-chloro-Abz, 3,5-dibromo-Abz, 6-amino-nicotinic acid, 2-amino-nicotinic acid, 2-chloronicotinic acid, niflumic acid and fluorogenic derivatives thereof; and wherein Z is selected from tryptophan, tyrosine, phenylalanine, p-nitrophenylalanine, m-nitrophenylalanine, DABSYL, DABCYL and halogenated derivatives thereof.

A compound of Formula II of particular interest is DABCYL-γ-Abu-Gly-Val-Val-Asn-Ala-Ser-Ala-Arg-Leu-Ala-EDANS (designated DE2) [SEQ ID NO:32].

Within Formula I there is a second subclass of compounds of high interest represented by Formula III Z—W—Val—Val—Asn—Ala—Ser—Ala—Arg—Leu—Y (III)
[SEQ ID NO: 33]

wherein W is an aminoalkylcarboxylic acid; wherein one of Y and Z is a fluorogenic radical and the other is an acceptor radical.

A preferred class of compounds consists of those compounds of Formula III wherein W is a lower aminoalkylcarboxylic acid; wherein Y is a fluorogenic radical; and wherein Z is an acceptor radical.

A more preferred class of compounds consists of those compounds of Formula III wherein W is selected from glycine, 4-aminobutyric acid, 5-aminopentanoic acid, 6-aminocaproic acid and 7-aminoheptanoic acid; wherein Y is selected from EDANS, Abz, DANSYL, nicotinic acid, 4-guanidino-benzoic acid, N-methyl-Abz, 4-chloro-Abz, 5-chloro-Abz, 6-chloro-Abz, 3,5-dibromo-Abz, 6-amino-nicotinic acid, 2-amino-nicotinic acid, 2-chloronicotinic acid, niflumic acid and fluorogenic derivatives thereof; and wherein Z is selected from tryptophan, tyrosine, phenylalanine, p-nitrophenylalanine, m-nitrophenylalanine, DABSYL, DABCYL and halogenated derivatives thereof.

A compound of Formula III of particular interest is DABCYL-γ-Abu-Val-Val-Asn-Ala-Ser-Ala-Arg-Leu-EDANS (designated DE1) [SEQ ID NO:34].

An amino acid sequence sufficient for substrate recognition by a herpesvirus protease includes "maturation" cleavage site sequences and "release" cleavage site sequences of herpesvirus protease substrates. These include "maturation" and "release" cleavage site sequences for HCMV, HSV-1, HSV-2, VZV, HHV-6, HHV-7 and EBV proteases. The preferred novel substrates are based on a HCMV "maturation" cleavage site sequence (Val-Ala-Glu-Arg-Ala-Gln-Ala-Gly-Val-Val-Asn-Ala*Ser-CYs-Arg-Leu-Ala-Thr-Ala [SEQ ID NO:35], where "*" denotes the cleavage site) at the C-terminus of the capsid assembly protein. Peptides of various lengths encompassing this sequence, or homologs thereof, provide amino acid sequences sufficient for substrate recognition by a herpesvirus protease. Preferably peptides have between six amino acids and twelve amino acids. This length also provides an adequate distance for the acceptor radical to intramolecularly quench the fluorogenic radical. Two sequences, an octapeptide -Val-Val-Asn-Ala-Ser-Ala-Arg-Leu- [SEQ ID NO:1]and a decapeptide -Gly-Val-Val-Asn-Ala-Ser-Ala-Arg-Leu-Ala- [SEQ ID NO:5]are even more preferred.

The fluorometric assay developed to incorporate the substrate compounds of the invention is a method for the determination of a herpesvirus protease and inhibitors of a herpesvirus protease, e.g. a CMV protease (also known as assemblin) encoded by $U_L80$, which comprises placing a known amount of the herpesvirus protease in the wells of a "Microlite 1"96 well plate (Dynatek Laboratories, Inc.), adding a known amount of the substrate at 22° C., measuring the change in fluorescence with time and determining the molar velocity of the herpesvirus protease by comparing against a standard curve which relates changes in fluorescent intensity to changes in concentration of product. Potential inhibitors of the protease action can be added to the well to observe their effect on the protease cleavage activity.

Besides variations in the fluorescence donor and acceptor radicals, the amino acids in the substrate sequences can be varied to optimize the affinity and kinetic properties for the particular herpesvirus protease under consideration. In the case of assemblin, valine (P3 - Val) can be replaced by Leu, Phe and other hydrophobic residues. Leucine (P4'- Leu) can similarly be substituted with Val and other hydrophobic residues. Cysteine (P2'- Cys) can be replaced with Ala.

The acceptor radical can be located at other positions in the N-terminal section of the sequence such as by replacing Val (P3) with a modified amino acid radical such as Phe(m-$NO_2$). The C-terminal acid can be replaced by an acceptor radical such as nitrobenzylamine as well. This may be necessary, in order to accommodate particular substrate requirements of a given herpesvirus protease. Attachment of aminobenzoic acid and substituted aminobenzoic acid radicals is preferred at the N-terminus, however, addition of a lysine amino acid at the C-terminus will allow their incorporation at the C-terminus portion of the substrate.

Where the term "fluorogenic donor" is used, it embraces a fluorescence emitting radical, such as anthracene, aminobenzoyl, indole, and aminoethylnaphthyl radicals, and the like, which can be modified and attached to the amino acid sequence. Such radicals include 5-[(2-aminoethyl)amino] naphthalene-1-sulfonic acid (EDANS), 2-aminobenzoic acid (Abz) and derivatives thereof, e.g. N-methyl-Abz, 4-chloro-Abz, 5-chloro-Abz, 6-chloro-Abz, 3,5-dibromo-Abz, 5-dimethylamino-naphthalene-1-sulfonyl (DANSYL) and derivatives thereof, nicotinic acid and derivatives thereof, such as 6-aminonicotinic acid, 2-aminonicotinic acid, 2-chloronicotinic acid, and niflumic acid, 4-guanidinobenzoic acid and derivatives of 4-guanidino-benzoic acid; and the like. The term "acceptor radical" embraces radicals which have a quenching aromatic radical which absorbs the fluorescence energy of the fluorogenic donor radical and reduces the fluorescence emission when the fluorogenic donor radical is covalently held in close proximity to the acceptor radical. Such "acceptor radicals" include 4-(4'-dimethylaminophenylazo)benzoyl (DABCYL), 4-(4'-dimethylaminophenylazo) phenylsulfonyl (DABSYL), dinitrophenol (DNP), or an amino acid derivative such as tryptophan (Trp), tyrosine (Tyr), phenylalanine (Phe), p-nitrophenylalanine [Phe(p-$NO_2$)], nitrotyrosine, m-nitrophenylalanine [Phe(m-$NO_2$)], and halogenated derivatives thereof. The term "aminoalkylcarboxylic acids" embraces radicals which can be included between either the fluorescing donor radical or the acceptor radical, and the peptide sequences. Such radicals act as spacers and reduce the possibility of the fluorescing donor radical or the acceptor radical, having a steric or other negative effect on the binding of the substrate and the enzyme. Such aminoalkylcarboxylic acids embrace linear or branched radicals having one to about twenty carbon atoms or, preferably, one to about twelve carbon atoms. More preferred aminoalkylcarboxylic acids radicals are "lower aminoalkylcarboxylic acids" radicals having one to about ten carbon atoms. Most preferred are lower aminoalkylcarboxylic acids radicals having one to about seven carbon atoms. Examples of such radicals include glycine, 4-aminobutyric acid, 5-aminopentanoic acid, 6-aminocaproic acid, 7-aminoheptanoic acid, and the like.

It will be appreciated that various modifications can be made to the aforesaid preferred fluorogenic substrates to provide substantially similar useful results in the fluorometric assay for herpesvirus protease.

While the specification concludes with claims particularly pointing out and distinctly claiming the subject matter regarded as forming the present invention, it is believed that the invention will be better understood from the following detailed description of preferred embodiments of the invention taken in conjunction with the appended drawings, in which, briefly:

FIG. 1 is a graphical representation which shows the fluorescence emission spectra of 2 μM substrate DE1 [SEQ ID NO:34]and 2 μM Ser-Ala-Arg-Leu-EDANS (the C-terminal cleavage product) [SEQ ID NO:36]. Fluorescence magnitude is plotted versus wavelength in nm.

FIG. 2 is a graphical representation which shows the time course of change in fluorescence emission spectra during hydrolysis of substrate DE1 [SEQ ID NO:34]by CMV assemblin. The arrow indicates the addition of protease to 10 μM DE1 [SEQ ID NO:34]. The cleavage of the substrate resulted in a 10-fold increase in fluorescence emission at 340 nm excitation and 480 nm emission wavelength within 30 minutes. Fluorescence magnitude is plotted versus time.

GENERAL SYNTHETIC PROCEDURES

The preferred novel fluorogenic substrates of this invention and their analogs can be made by known solution and solid phase peptide synthesis methods but modified to incorporate the acceptor radical, e.g. DABCYL at the N-terminal position, the fluorogenic radical, e.g. EDANS at the C terminus and spacer radicals between the peptide and the acceptor radical or the fluorogenic radical. The preferred peptide synthesis method follows conventional Merrifield solid-phase procedure [*J.Amer. Chem. Soc.*, 85, 2149 (1963); *Science*, 150, 178 (1965) modified by the procedure of Tam et al., *J. Amer. Chem. Soc.*, 105, 6442 (1983)].

In order to illustrate specific preferred embodiments of the invention in greater detail, the following exemplary laboratory preparative work was carried out. It should be understood that the invention is not limited to these specific examples.

Solid phase synthesis of assemblin substrates are prepared by conventional solid phase peptide synthesis using an appropriate Boc-amino acid phenylacetamidomethyl (PAM) resin. For each synthesis, 0.5 grams of resin was used (0.5 mmole). The following synthetic protocol is an example of that can be used for incorporation of the Bocamino acids.

| Deprotection: | |
|---|---|
| 50% trifluoroacetic acid/$CH_2Cl_2$ 5 minutes/25 minutes | |
| $CH_2CL_2$ | 2 × 1 minutes |
| Isopropanol | 2 × 1 minutes |
| $CH_2Cl_2$ | 2 × 1 minutes |
| Neutralization: | |
| 10% diisopropylethylamine/$CH_2Cl_2$ 3 minutes/5 minutes | |
| $CH_2Cl_2$ | 2 × 1 minutes |
| DMF | 2 × 1 minutes |

Amino acids are coupled to the resin, or the growing peptide chain on the resin, by adding 4-equivalents of butyloxycarbonyl (Boc) protected amino acid and 4 equivalents of diisopropylcarbodiimide (DCC) in the presence of 4 equivalents of hydroxybenzotriazole (HOBT) in dimethylformamide (DMF) for 2 hours. 4-(4'-Dimethylamiphenylazo)benzoyl (DABCYL) is obtained from Sigma as the free acid and coupled in the regular fashion. Completed peptides are cleaved by the hydrofluoric acid (HF)/anisole 9:1 procedure of Tam et al., *J.Amer. Chem. Soc.*, 105, 6442 (1983). Crude DABCYL-peptides are dissolved in 20% acetic acid and lyophilized. Crude peptides are purified by reverse-phase HPLC on a $C_{18}$ semipreparative column using a 0.1% trifluoroacetic acid (TFA) and acetonitrile gradient. The EDANS radical was coupled to DABCYL-peptide free acid in DMF by adding a 5 times molar excess of EDANS in the presence of benzotriazolyl-N-oxytris(dimethylamino)-phosphonium hexafluorophosphate (BOP) and diisopropylethylamine (DIPEA). The mixture was filtered and diluted with 5 mL 50% acetic acid and 20 mL water. Crude DABCYL/EDANS-peptides are purified by reverse-phase HPLC on a $C_{18}$ semipreparative column using a 0.1% TFA and acetonitrile gradient. Their identity was confirmed by high-resolution mass spectrometry and amino acid analysis.

EXAMPLE 1

Purified DABCYL-γ-Abu-peptide free acid (24 mg, 20 μmol) was dissolved in 5 mL DMF and coupled with 28.8 mg (100 μmol) EDANS in the presence of 44 mg (100 μmol) BOP and 35 μL (200 μmol) DIPEA for 12 hours. The reaction mixture was filtered and diluted with 5 mL 50% acetic acid and 20 mL water. This solution was purified on HPLC using acetonitrile/water (0.1% TFA) gradient (20–50% acetonitrile in 30 minutes). The identity of DABCYL-γ-Abu-Val-Val-Asn-Ala-Ser-Ala-Arg-Leu-EDANS (DE1) [SEQ ID NO:34]was confirmed by amino acid analysis and FAB mass spectrometry. FAB MS: (M+H)+=1413.8

EXAMPLE 2

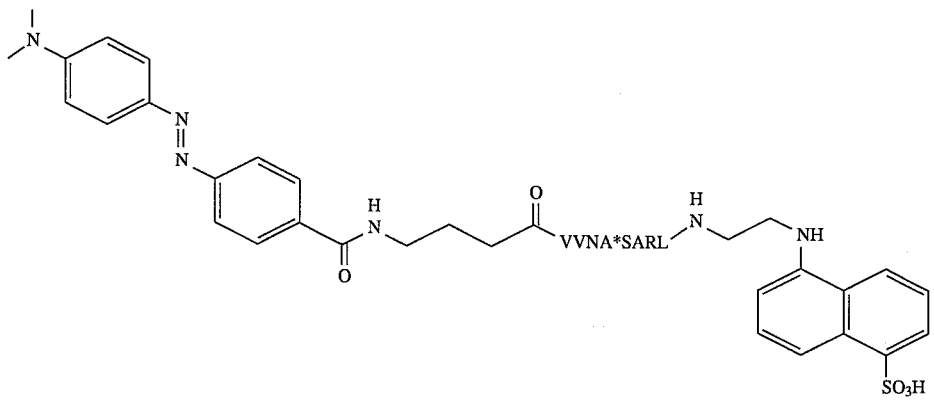

DABCYL-γ-Abu-Val-Val-Asn-Ala-Ser-Ala-Arq-Leu-EDANS (DE1) [SEQ ID NO:34]

DABCYL-γ-Abu-Val-Val-Asn-Ala-Ser-Ala-Arg-Leu-EDANS (DE1) [SEQ ID NO:34]was synthesized on an Applied Biosystems peptide synthesizer (Model 430A)

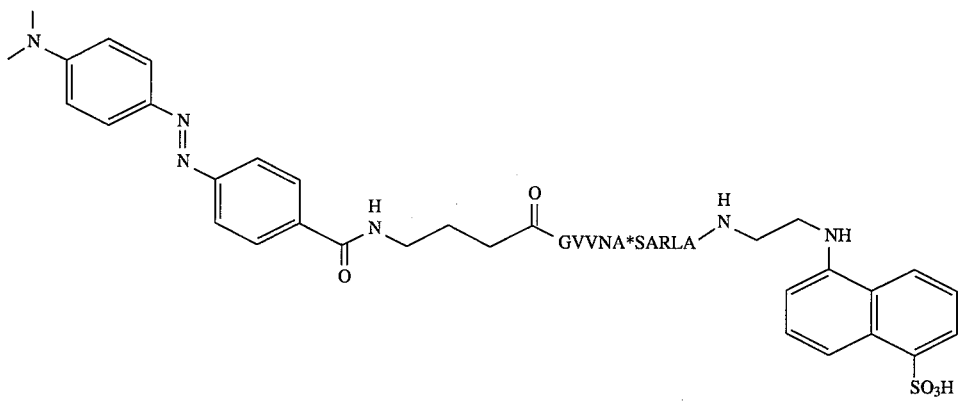

DABCYL-γ-Abu-Gly-Val-Val-Asn-Ala-Ser-Ala-Arq-Leu-Ala-EDANS (DE2) [SEQ ID NO: 32 ]

DABCYL-γ-Abu-Gly-Val-Val-Asn-Ala-Ser-Ala-Arg-Leu-Ala-EDANS (DE2) [SEQ ID NO:32]was synthesized on an Applied Biosystems peptide synthesizer (Model 430A) using a standard synthesis protocol, starting with 0.5 using a standard synthesis protocol, starting with 0.5 mmol Boc-Leu-PAM resin. The fully protected DABCYL-γ-Abu-peptide resin was cleaved and deprotected with treatment of HF/anisole (9:1) at 0° C. for 1 hour. Crude DABCYL-γ-Abu-peptide was purified on HPLC using acetonitrile/water (0.1% TFA) gradient (20–50% acetonitrile in 30 minutes).

mmol Boc-Ala-PAM resin. The fully protected DABCYL-γ-Abu-peptide resin was cleaved and deprotected with treatment of HF/anisole (9:1) at 0° C. for 1 hour. Crude DABCYL-γ-Abu-peptide was purified on HPLC using acetonitrile/water (0o1% TFA) gradient (20–50% acetonitrile in 30 minutes). Purified DABCYL-γ-Abu-peptide free acid in 5 mL DMF (26 mg, 20 µmol) was coupled with 28.8 mg (100 µmol) EDANS in the presence of 44 mg (100 µmol) BOP and 35 µL (200 µmol) DIPEA for 12 hour. The reaction mixture was filtered and diluted with 5 mL 50% acetic acid and 20 mL water. This solution was purified on HPLC using acetonitrile/water (0.1% TFA) gradient (20–50% acetonitrile in 30 minutes). The identity of DABCYL-γ-Abu-Gly-Val-Val-Asn-Ala-Ser-Ala-Arg-Leu-Ala-EDANS (DE2) [SEQ ID NO:32]was confirmed by amino acid analysis and FAB mass spectrometry. FAB MS: (M+H)+=1541.8

The emission spectra of DE1 [SEQ ID NO:34]and its C-terminal cleavage product, Ser-Ala-Arg-Leu-EDANS [SEQ ID NO:38], were measured on a Perkin-Elmer LS50 spectrophotometer. The substrates of the invention showed a small amount of fluorescent background due to incomplete quenching of the fluorogenic donor radical. As shown in FIG. 1, the C-terminal cleavage product had a broad emssion maximum between 470 nm and 490 nm and the fluorescence magnitude was 20-fold greater that of an equal concentration of DE1 [SEQ ID NO:34].

An assay was developed for screening potential herpesvirus protease inhibitors utilizing the substrates of the invention. Recombinant HCMV protease was purified from *E. coli* expressing a DNA construction encoding the protease domain of the $U_L80$ open reading frame of human cytomegalovirus strain AD169. The construction also encoded six additional histidine residues at the amino terminus of the protease. These additional histidine residues provided an affinity ligand by which it was purified using nickel-nitriloacetic acidagarose (Qiagen).

The purified protease was stored as a 1–3 mg/ml stock solution in 50 mM sodium phosphate buffer, pH 7.4; 300 mM sodium chloride; 100 mM imidazole; 50% (v/v) glycerol. This stock was diluted with assay buffer to 4.8 µg/ml. A 100 µL aliquot of this solution was used in the enzyme reaction.

A specific substrate was synthesized based on the cleavage specificity of HCMV protease at the "maturation" site of the assembly protein. Upon excitation at 360 nm the EDANS chromophore emitted light (fluoresces) at 490 nm that was absorbed by the DABCYL chromophore ($E_{max}$=460 nm). However, when the two chromophores were separated because of hydrolysis of the peptide moiety by HCMV protease, the EDANS fluorescence was no longer quenched and an increase in fluorescence was realized. Substrate was stored as a stock solution at 160 µg/ml in dimethyl sulfoxide. This was diluted 10-fold with assay buffer to give a concentration of 16 µg/ml just before use. An aliquot of 50 µL was used in the reaction An assay Buffer (10 mM sodium phosphate buffer, pH 7.4; 150 mM sodium acetate; 0.1% CHAPS; and 20% (v/v) glycerol) was used to dilute stock solutions of enzyme and substrate.

Inhibitors were dissolved in dimethyl sulfoxide at 16-times the final assay concentration. A 10 µL aliquot of this inhibitor solution was used in the reaction.

A 100 µL aliquot of enzyme solution (4.8 g/ml) was mixed with 10 µL of inhibitor solution in a 96-well plate and incubated at 22° C. for 30 minutes. Control reactions contained 10 µL of dimethylsulfoxide instead of inhibitor solution. After the preincubation was completed, 50 µL of substrate solution was added and the fluorescence recorded every 5 minutes for a period of 30 minutes. All reactions were run in triplicate with the exception of the uninhibited control reaction which was replicated 6-fold. The change in fluorescence was recorded over time and an average rate for each set of 3 reactions was calculated. Fluorescence values were subject to spurious variations due to factors such as dust in the 96well plate; such results were omitted from the calculation of relative rates.

Although this invention has been described with respect to specific embodiments, the details of these embodiments are not to be construed as limitations.

---

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Z- W
        / note="Z=a fluorogenic donor or acceptor radical
        which precedes the amino acid at position 1. W=an
        aminoalkylcarboxylic acid which may or may not be
        inserted between Z and the amino acid at position 1."

( i x ) FEATURE:
        ( A ) NAME/KEY: Modified-site
        ( B ) LOCATION: 2
        ( D ) OTHER INFORMATION: /note="Xaa at position 2 is any hydrophobic amino acid."

( i x ) FEATURE:
  ( A ) NAME/KEY: Modified-site
  ( B ) LOCATION: 6
  ( D ) OTHER INFORMATION: /note="Xaa at position 6 is Ala or Cys."

( i x ) FEATURE:
  ( A ) NAME/KEY: Modified-site
  ( B ) LOCATION: 8
  ( D ) OTHER INFORMATION: /label=V- Y
    / note="Xaa at position 8 is any hydrophobic amino acid. Y=a fluorogenic donor or acceptor radical which follows the amino acid at position 8. V=an aminoalkylcarboxylic acid which may or may not be inserted between Y and Xaa at position 8."

( x i ) SEQUENCE DESCRIPTION: SEQ ID NO:1:

Val Xaa Asn Ala Ser Xaa Arg Xaa
1               5

( 2 ) INFORMATION FOR SEQ ID NO:2:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=Z- W
      / note="Z=a fluorogenic donor or acceptor radical which precedes the amino acid at position 1. W=an aminoalkylcarboxylic acid which may or may not be inserted between Z and the amino acid at position 1."

( i x ) FEATURE:
    ( A ) NAME/KEY: Modified-site
    ( B ) LOCATION: 3
    ( D ) OTHER INFORMATION: /note="Xaa at position 3 is any hydrophobic amino acid."

( i x ) FEATURE:
    ( A ) NAME/KEY: Modified-site
    ( B ) LOCATION: 7
    ( D ) OTHER INFORMATION: /note="Xaa at position 6 is Ala or Cys."

( i x ) FEATURE:
    ( A ) NAME/KEY: Modified-site
    ( B ) LOCATION: 9
    ( D ) OTHER INFORMATION: /label=V- Y
      / note="Xaa at position 8 is any hydrophobic amino acid. Y=a fluorogenic donor or acceptor radical which follows the amino acid at position 8. V=an aminoalkylcarboxylic acid which may or may not be inserted between Y and Xaa at position 8."

( x i ) SEQUENCE DESCRIPTION: SEQ ID NO:2:

Gly Val Xaa Asn Ala Ser Xaa Arg Xaa
1                   5

( 2 ) INFORMATION FOR SEQ ID NO:3:

( i ) SEQUENCE CHARACTERISTICS:
    ( A ) LENGTH: 9 amino acids
    ( B ) TYPE: amino acid
    ( D ) TOPOLOGY: linear ( i i ) MOLECULE TYPE: peptide ( i x ) FEATURE:

(A) NAME/KEY: Modified-site
(B) LOCATION: 1
(D) OTHER INFORMATION: /label=Z- W
/ note="Z=a fluorogenic donor or acceptor radical which precedes the amino acid at position 1. W=an aminoalkylcarboxylic acid which may or may not be inserted between Z and the amino acid at position 1."

(ix) FEATURE:
(A) NAME/KEY: Modified-site
(B) LOCATION: 2
(D) OTHER INFORMATION: /note="Xaa at position 2 is any hydrophobic amino acid."

(ix) FEATURE:
(A) NAME/KEY: Modified-site
(B) LOCATION: 6
(D) OTHER INFORMATION: /note="Xaa at position 6 is Ala or Cys."

(ix) FEATURE:
(A) NAME/KEY: Modified-site
(B) LOCATION: 8
(D) OTHER INFORMATION: /note="Xaa at position 8 is any hydrophobic amino acid."

(ix) FEATURE:
(A) NAME/KEY: Modified-site
(B) LOCATION: 9
(D) OTHER INFORMATION: /label=V- Y
/ note="Y=a fluorogenic donor or acceptor radical which follows the amino acid at position 9. V=an aminocarboxylic acid which may or may not be inserted between Y and amino acid at position 9."

(xi) SEQUENCE DESCRIPTION: SEQ ID NO:3:

Val Xaa Asn Ala Ser Xaa Arg Xaa Ala
1               5

(2) INFORMATION FOR SEQ ID NO:4:

(i) SEQUENCE CHARACTERISTICS:
(A) LENGTH: 10 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Z- W
/ note="Z=a fluorogenic donor or acceptor radical which precedes the amino acid at position 1. W=an aminoalklylcarboxylic acid which may or may not be inserted between Z and the amino acid at position 1."

(ix) FEATURE:
(A) NAME/KEY: Modified-site
(B) LOCATION: 4
(D) OTHER INFORMATION: /note="Xaa at position 4 is any hydrophic amino acid."

(ix) FEATURE:
(A) NAME/KEY: Modified-site
(B) LOCATION: 8
(D) OTHER INFORMATION: /note="Xaa at position 8 is Ala or Cys."

(ix) FEATURE:
(A) NAME/KEY: Modified-site
(B) LOCATION: 10
(D) OTHER INFORMATION: /label=V- Y
/ note="Xaa at position 10 is any hydrophobic amino acid. Y=a fluorogenic donor or acceptor radical which follows Xaa at position 10. V= an aminoalkylcarboxylic acid which may or may not be inserted between Y and Xaa at position 10."

( x i ) SEQUENCE DESCRIPTION: SEQ ID NO:4:

Ala Gly Val Xaa Asn Ala Ser Xaa Arg Xaa
1               5                       10

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Z- W
            / note="Z=a fluorogenic donor or acceptor radical
            which precedes the amino acid at position 1. W=an
            aminoalkylcarboxylic acid which may or may not be
            inserted between Z and the amino acid at position 1."

( i x ) FEATURE:
        ( A ) NAME/KEY: Modified-site
        ( B ) LOCATION: 3
        ( D ) OTHER INFORMATION: /note="Xaa at position 3 is any
            hydrophobic amino acid."

( i x ) FEATURE:
        ( A ) NAME/KEY: Modified-site
        ( B ) LOCATION: 7
        ( D ) OTHER INFORMATION: /note="Xaa at position 7 is Ala or
            Cys."

( i x ) FEATURE:
        ( A ) NAME/KEY: Modified-site
        ( B ) LOCATION: 9
        ( D ) OTHER INFORMATION: /note="Xaa at position 9 is any
            hydrophobic amino acid."

( i x ) FEATURE:
        ( A ) NAME/KEY: Modified-site
        ( B ) LOCATION: 10
        ( D ) OTHER INFORMATION: /label=V- Y
            / note="Y=a fluorogenic donor or acceptor radical
            which follows the amino acid at position 10. V=an
            aminoalkylcarboxylic acid which may or may not be
            inserted between Y and the amino acid at position 10."

( x i ) SEQUENCE DESCRIPTION: SEQ ID NO:5:

Gly Val Xaa Asn Ala Ser Xaa Arg Xaa Ala
1               5                       10

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Z- W
            / note="Z=a fluorogenic donor or acceptor radical
            which precedes the amino acid at position 1. W=an
            aminoalkylcarboxylic acid which may or may not be
            inserted between Z and the amino acid at position 1."

( i x ) FEATURE:
        ( A ) NAME/KEY: Modified-site
        ( B ) LOCATION: 2
        ( D ) OTHER INFORMATION: /note="Xaa at position 2 is any hydrophobic amino acid."

( i x ) FEATURE:
    ( A ) NAME/KEY: Modified-site
    ( B ) LOCATION: 6
    ( D ) OTHER INFORMATION: /note="Xaa at position 6 is Ala or Cys."

( i x ) FEATURE:
    ( A ) NAME/KEY: Modified-site
    ( B ) LOCATION: 8
    ( D ) OTHER INFORMATION: /note="Xaa at position 8 is any hydrophobic residue."

( i x ) FEATURE:
    ( A ) NAME/KEY: Modified-site
    ( B ) LOCATION: 10
    ( D ) OTHER INFORMATION: /label=V- Y
        / note="Y=a fluorogenic donor or acceptor radical which follows the amino acid at position 10. V=an aminoalkylcarboxylic acid which may or may not be inserted between Y and the amino acid at position 10."

( x i ) SEQUENCE DESCRIPTION: SEQ ID NO:6:

Val Xaa Asn Ala Ser Xaa Arg Xaa Ala Thr
1               5                        10

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Z- W
            / note="Z=a fluorogenic donor or acceptor radical which precedes the amino acid at position 1. W=an aminoalkylcarboxylic acid which may or may not be inserted between Z and the amino acid at position 1."

( i x ) FEATURE:
        ( A ) NAME/KEY: Modified-site
        ( B ) LOCATION: 5
        ( D ) OTHER INFORMATION: /note="Xaa at position 5 is any hydrophobic amino acid."

( i x ) FEATURE:
        ( A ) NAME/KEY: Modified-site
        ( B ) LOCATION: 9
        ( D ) OTHER INFORMATION: /note="Xaa at position 9 is Ala or Cys."

( i x ) FEATURE:
        ( A ) NAME/KEY: Modified-site
        ( B ) LOCATION: 11
        ( D ) OTHER INFORMATION: /label=V- Y
            / note="Xaa at position 11 is any hydrophobic amino acid. Y=a fluorogenic donor or acceptor radical which follows Xaa at position 11. V= an aminoalkylcarboxylic acid which may or may not be inserted between Y and Xaa at position 11."

( x i ) SEQUENCE DESCRIPTION: SEQ ID NO:7:

Gln Ala Gly Val Xaa Asn Ala Ser Xaa Arg Xaa
1                     5                         10

( 2 ) INFORMATION FOR SEQ ID NO:8:

( i ) SEQUENCE CHARACTERISTICS:

(A) LENGTH: 11 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(D) OTHER INFORMATION: /label=Z- W
/note="Z=a fluorogenic donor or acceptor radical
which precedes the amino acid at position 1. W=an
aminoalkylcarboxylic acid which may or may not be
inserted between Z and the amino acid at position 1."

(i x) FEATURE:
(A) NAME/KEY: Modified-site
(B) LOCATION: 4
(D) OTHER INFORMATION: /note="Xaa at position 4 is any
hydrophobic amino acid."

(i x) FEATURE:
(A) NAME/KEY: Modified-site
(B) LOCATION: 8
(D) OTHER INFORMATION: /note="Xaa at position 8 is Ala or
Cys."

(i x) FEATURE:
(A) NAME/KEY: Modified-site
(B) LOCATION: 10
(D) OTHER INFORMATION: /note="Xaa at position 10 is any
hydrophobic amino acid."

(i x) FEATURE:
(A) NAME/KEY: Modified-site
(B) LOCATION: 11
(D) OTHER INFORMATION: /label=V- Y
/note="Y=a fluorogenic donor or acceptor radical
which follows the amino acid at position 11. V=an
aminoalkylcarboxylic acid which may or may not be
inserted between Y and the amino acid at position 11."

(x i) SEQUENCE DESCRIPTION: SEQ ID NO:8:

Ala Gly Val Xaa Asn Ala Ser Xaa Arg Xaa Ala
1               5                   10

(2) INFORMATION FOR SEQ ID NO:9:

(i) SEQUENCE CHARACTERISTICS:
(A) LENGTH: 11 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(D) OTHER INFORMATION: /label=Z- W
/note="Z=a fluorogenic donor or acceptor radical
which precedes the amino acid at position 1. W=an
aminoalkylcarboxylic acid which may or may not be
inserted between Z and the amino acid at position 1."

(i x) FEATURE:
(A) NAME/KEY: Modified-site
(B) LOCATION: 3
(D) OTHER INFORMATION: /note="Xaa at position 3 is any
hydrophobic amino acid."

(i x) FEATURE:
(A) NAME/KEY: Modified-site
(B) LOCATION: 7
(D) OTHER INFORMATION: /note="Xaa at position 7 is Ala or
Cys."

(i x) FEATURE:
(A) NAME/KEY: Modified-site (B) LOCATION: 9
(D) OTHER INFORMATION: /note="Xaa at position 9 is any hydrophobic amino acid."

(ix) FEATURE:
(A) NAME/KEY: Modified-site
(B) LOCATION: 11
(D) OTHER INFORMATION: /label=V- Y
/ note="Y=a fluorogenic donor or acceptor radical which follows the amino acid at position 11. V=an aminoalkylcarboxylic acid which may or may not be inserted between Y and the amino acid at position 11."

(xi) SEQUENCE DESCRIPTION: SEQ ID NO:9:

Gly Val Xaa Asn Ala Ser Xaa Arg Xaa Ala Thr
1               5                   10

(2) INFORMATION FOR SEQ ID NO:10:

(i) SEQUENCE CHARACTERISTICS:
(A) LENGTH: 11 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Z- W
/ note="Z=a fluorogenic donor or acceptor radical which precedes the amino acid at position 1. W=an aminoalkylcarboxylic acid which may or may not be inserted between Z and the amino acid at position 1."

(ix) FEATURE:
(A) NAME/KEY: Modified-site
(B) LOCATION: 2
(D) OTHER INFORMATION: /note="Xaa at position 2 is any hydrophobic amino acid."

(ix) FEATURE:
(A) NAME/KEY: Modified-site
(B) LOCATION: 6
(D) OTHER INFORMATION: /note="Xaa at position 6 is Ala or Cys."

(ix) FEATURE:
(A) NAME/KEY: Modified-site
(B) LOCATION: 8
(D) OTHER INFORMATION: /note="Xaa at position 8 is any hydrophobic amino acid."

(ix) FEATURE:
(A) NAME/KEY: Modified-site
(B) LOCATION: 11
(D) OTHER INFORMATION: /label=V- Y
/ note="Y=a fluorogenic donor or acceptor radical which follows the amino acid at position 11. V=an aminoalkylcarboxylic acid which may or may not be inserted between Y and the amino acid at position 11."

(xi) SEQUENCE DESCRIPTION: SEQ ID NO:10:

Val Xaa Asn Ala Ser Xaa Arg Xaa Ala Thr Ala
1               5                   10

(2) INFORMATION FOR SEQ ID NO:11:

(i) SEQUENCE CHARACTERISTICS:
(A) LENGTH: 12 amino acids
(B) TYPE: amino acid
(D) TOPOLOGY: linear (ii) MOLECULE TYPE: peptide ( i x ) FEATURE:
  ( A ) NAME/KEY: Modified-site
  ( B ) LOCATION: 1
  ( D ) OTHER INFORMATION: /label=Z- W
    / note="Z=a fluorogenic donor or acceptor radical
    which precedes the amino acid at position 1. W=an
    aminoalkylcarboxylic acid which may or may not be
    inserted between Z and the amino acid at position
    1."

( i x ) FEATURE:
  ( A ) NAME/KEY: Modified-site
  ( B ) LOCATION: 6
  ( D ) OTHER INFORMATION: /note="Xaa at position 6 is any
    hydrophobic amino acid."

( i x ) FEATURE:
  ( A ) NAME/KEY: Modified-site
  ( B ) LOCATION: 10
  ( D ) OTHER INFORMATION: /note="Xaa at position 10 is Ala
    or Cys."

( i x ) FEATURE:
  ( A ) NAME/KEY: Modified-site
  ( B ) LOCATION: 12
  ( D ) OTHER INFORMATION: /label=V- Y
    / note="Xaa at position 12 is any hydrophobic
    amino acid. Y=a fluorogenic donor or acceptor
    radical which follows the amino acid at position
    12. V=an aminoalkylcarboxylic acid which may or
    may not be inserted between Y and Xaa at position
    12."

( x i ) SEQUENCE DESCRIPTION: SEQ ID NO:11:

Ala Gln Ala Gly Val Xaa Asn Ala Ser Xaa Arg Xaa
1               5                   10

( 2 ) INFORMATION FOR SEQ ID NO:12:

( i ) SEQUENCE CHARACTERISTICS:
   ( A ) LENGTH: 12 amino acids
   ( B ) TYPE: amino acid
   ( D ) TOPOLOGY: linear ( i i ) MOLECULE TYPE: peptide ( i x ) FEATURE:
   ( A ) NAME/KEY: Modified-site
   ( B ) LOCATION: 1
   ( D ) OTHER INFORMATION: /label=Z- W
    / note="Z=a fluorogenic donor or acceptor radical
    which precedes the amino acid at position 1. W=an
    aminoalkylcarboxylic acid which may or may not be
    inserted between Z and the amino acid at position 1."

( i x ) FEATURE:
   ( A ) NAME/KEY: Modified-site
   ( B ) LOCATION: 5
   ( D ) OTHER INFORMATION: /note="Xaa at position 5 is any
    hydrophobic amino acid."

( i x ) FEATURE:
   ( A ) NAME/KEY: Modified-site
   ( B ) LOCATION: 9
   ( D ) OTHER INFORMATION: /note="Xaa at position 9 is Ala or
    Cys."

( i x ) FEATURE:
   ( A ) NAME/KEY: Modified-site
   ( B ) LOCATION: 11
   ( D ) OTHER INFORMATION: /note="Xaa at position 11 is any
    hydrophobic amino acid."

( i x ) FEATURE:
   ( A ) NAME/KEY: Modified-site
   ( B ) LOCATION: 12
   ( D ) OTHER INFORMATION: /label=V- Y / note="Y=a fluorogenic acceptor or donor radical
which follows the amino acid at position 12. V=an
aminoalkylcarboxylic acid which may or may not be
inserted between Y and the amino acid at position
12."

(x i) SEQUENCE DESCRIPTION: SEQ ID NO:12:

Gln Ala Gly Val Xaa Asn Ala Ser Xaa Arg Xaa Ala
1               5                   10

(2) INFORMATION FOR SEQ ID NO:13:

(i) SEQUENCE CHARACTERISTICS:
(A) LENGTH: 12 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(D) OTHER INFORMATION: /label=Z- W
/ note="Z=a fluorogenic donor or acceptor radical
which precedes the amino acid at position 1. W=an
aminoalkylcarboxylic acid which may or may not be
inserted between Z and the amino acid at position 1."

(i x) FEATURE:
(A) NAME/KEY: Modified-site
(B) LOCATION: 4
(D) OTHER INFORMATION: /note="Xaa at position 4 is
any hydrophobic amino acid."

(i x) FEATURE:
(A) NAME/KEY: Modified-site
(B) LOCATION: 8
(D) OTHER INFORMATION: /note="Xaa at position 8 is Ala or
Cys."

(i x) FEATURE:
(A) NAME/KEY: Modified-site
(B) LOCATION: 10
(D) OTHER INFORMATION: /note="Xaa at position 10 is any
hydrophobic amino acid."

(i x) FEATURE:
(A) NAME/KEY: Modified-site
(B) LOCATION: 12
(D) OTHER INFORMATION: /label=V- Y
/ note="Y=a fluorogenic donor or acceptor radical
which follows the amino acid at position 12. V=an
aminoalkylcarboxylic acid which may or may not be
inserted between Y and the amino acid at position
12."

(x i) SEQUENCE DESCRIPTION: SEQ ID NO:13:

Ala Gly Val Xaa Asn Ala Ser Xaa Arg Xaa Ala Thr
1               5                   10

(2) INFORMATION FOR SEQ ID NO:14:

(i) SEQUENCE CHARACTERISTICS:
(A) LENGTH: 12 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(D) OTHER INFORMATION: /label=Z- W
/ note="Z=a fluorogenic donor or acceptor radical
which precedes the amino acid at position 1. W=an
aminoalkylcarboxylic acid which may or may not be inserted between Z and the amino acid at position 1."

( i x ) FEATURE:
  ( A ) NAME/KEY: Modified-site
  ( B ) LOCATION: 3
  ( D ) OTHER INFORMATION: /note="Xaa at position 3 is any
         hydrophobic amino acid."

( i x ) FEATURE:
  ( A ) NAME/KEY: Modified-site
  ( B ) LOCATION: 7
  ( D ) OTHER INFORMATION: /note="Xaa at position 7 is Ala or
         Cys."

( i x ) FEATURE:
  ( A ) NAME/KEY: Modified-site
  ( B ) LOCATION: 9
  ( D ) OTHER INFORMATION: /note="Xaa at position 9 is any
         hydrophobic amino acid."

( i x ) FEATURE:
  ( A ) NAME/KEY: Modified-site
  ( B ) LOCATION: 12
  ( D ) OTHER INFORMATION: /label=V- Y
         / note="Y=a fluorogenic donor or acceptor radical
         which follows the amino acid at position 12. V=an
         aminoalkylcarboxylic acid which may or may not be
         inserted between Y and the amino acid at position
         12."

( x i ) SEQUENCE DESCRIPTION: SEQ ID NO:14:

Gly Val Xaa Asn Ala Ser Xaa Arg Xaa Ala Thr Ala
1               5                   10

( 2 ) INFORMATION FOR SEQ ID NO:15:

( i ) SEQUENCE CHARACTERISTICS:
    ( A ) LENGTH: 13 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=Z- W
           / note="Z=a fluorogenic donor or acceptor radical
           which precedes the amino acid at position 1. W=an
           aminoalkylcarboxylic acid which may or may not be
           inserted between Z and the amino acid at position 1."

( i x ) FEATURE:
    ( A ) NAME/KEY: Modified-site
    ( B ) LOCATION: 7
    ( D ) OTHER INFORMATION: /note="Xaa at position 7 is any
           hydrophobic amino acid."

( i x ) FEATURE:
    ( A ) NAME/KEY: Modified-site
    ( B ) LOCATION: 11
    ( D ) OTHER INFORMATION: /note="Xaa at position 11 is Ala
           or Cys."

( i x ) FEATURE:
    ( A ) NAME/KEY: Modified-site
    ( B ) LOCATION: 13
    ( D ) OTHER INFORMATION: /label=V- Y
           / note="Xaa at position 13 is any hydrophobic
           amino acid. Y=a fluorogenic donor or acceptor
           radical which follows Xaa at position 13. V=
           an aminoalkylcarboxylic acid which may or may
           not be inserted between Y and Xaa at position
           13."

( x i ) SEQUENCE DESCRIPTION: SEQ ID NO:15:

Arg Ala Gln Ala Gly Val Xaa Asn Ala Ser Xaa Arg Xaa (2) INFORMATION FOR SEQ ID NO:16:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Z- W
            /note="Z=a fluorogenic donor or acceptor radical
            which precedes the amino acid at position 1. W=an
            aminoalkylcarboxylic acid which may or may not be
            inserted between Z and the amino acid at position 1."

(ix) FEATURE:
        (A) NAME/KEY: Modified-site
        (B) LOCATION: 6
        (D) OTHER INFORMATION: /note="Xaa at position 6 is any
            hydrophobic amino acid."

(ix) FEATURE:
        (A) NAME/KEY: Modified-site
        (B) LOCATION: 10
        (D) OTHER INFORMATION: /note="Xaa at position 10 is Ala
            or Cys."

(ix) FEATURE:
        (A) NAME/KEY: Modified-site
        (B) LOCATION: 12
        (D) OTHER INFORMATION: /note="Xaa at position 12 is any
            hydrophobic amino acid."

(ix) FEATURE:
        (A) NAME/KEY: Modified-site
        (B) LOCATION: 13
        (D) OTHER INFORMATION: /label=V- Y
            /note="Y=a fluorogenic donor or acceptor radical
            which follows the amino acid at position 13. V=an
            aminoalkylcarboxylic acid which may or may be
            inserted between Y and the amino acid at position
            13."

(xi) SEQUENCE DESCRIPTION: SEQ ID NO:16:

Ala Gln Ala Gly Val Xaa Asn Ala Ser Xaa Arg Xaa Ala
1               5                   10

(2) INFORMATION FOR SEQ ID NO:17:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Z- W
            /note="Z=a fluorogenic donor or acceptor radical
            which precedes the amino acid at position 1. W=an
            aminoalkylcarboxylic acid which may or may not be
            inserted between Z and the amino acid at position
            1."

(ix) FEATURE:
        (A) NAME/KEY: Modified-site
        (B) LOCATION: 5
        (D) OTHER INFORMATION: /note="Xaa at position 5 is any
            hydrophobic amino acid."

( i x ) FEATURE:
        ( A ) NAME/KEY: Modified-site
        ( B ) LOCATION: 9
        ( D ) OTHER INFORMATION: /note="Xaa at position 9 is Ala or
                Cys."

( i x ) FEATURE:
        ( A ) NAME/KEY: Modified-site
        ( B ) LOCATION: 11
        ( D ) OTHER INFORMATION: /note="Xaa at position 11 is any
                hydrophobic amino acid."

( i x ) FEATURE:
        ( A ) NAME/KEY: Modified-site
        ( B ) LOCATION: 13
        ( D ) OTHER INFORMATION: /label=V-Y
                / note="Y=a fluorogenic donor or acceptor radical
                which follows the amino acid at position 13. V=an
                aminoalkylcarboxylic acid which may or may not be
                inserted between Y and the amino acid at position
                13."

( x i ) SEQUENCE DESCRIPTION: SEQ ID NO:17:

Gln Ala Gly Val Xaa Asn Ala Ser Xaa Arg Xaa Ala Thr
1                  5                                10

( 2 ) INFORMATION FOR SEQ ID NO:18:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Z-W
                / note="Z=a fluorogenic donor or acceptor radical
                which precedes the amino acid at position 1. W=an
                aminoalkylcarboxylic acid which may or may not be
                inserted between Z and the amino acid at position
                1."

( i x ) FEATURE:
        ( A ) NAME/KEY: Modified-site
        ( B ) LOCATION: 4
        ( D ) OTHER INFORMATION: /note="Xaa at position 4 is any
                hydrophobic amino acid."

( i x ) FEATURE:
        ( A ) NAME/KEY: Modified-site
        ( B ) LOCATION: 8
        ( D ) OTHER INFORMATION: /note="Xaa at position 8 is Ala or
                Cys."

( i x ) FEATURE:
        ( A ) NAME/KEY: Modified-site
        ( B ) LOCATION: 10
        ( D ) OTHER INFORMATION: /note="Xaa at position 10 is any
                hydrophobic amino acid."

( i x ) FEATURE:
        ( A ) NAME/KEY: Modified-site
        ( B ) LOCATION: 13
        ( D ) OTHER INFORMATION: /label=V-Y
                / note="Y=a fluorogenic donor or acceptor radical
                which follows the amino acid at position 18. V=an
                aminoalkylcarboxylic acid which may or may not be
                inserted between Y and the amino acid at position
                18."

( x i ) SEQUENCE DESCRIPTION: SEQ ID NO:18:

Ala Gly Val Xaa Asn Ala Ser Xaa Arg Xaa Ala Thr Ala
1                  5                                10

(2) INFORMATION FOR SEQ ID NO:19:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Z- W
            / note="Z=a fluorogenic donor or acceptor radical
            which precedes the amino acid at position 1. W=an
            aminoalkylcarboxylic acid which may or may not be
            inserted between Z and the amino acid at position
            1."

(ix) FEATURE:
        (A) NAME/KEY: Modified-site
        (B) LOCATION: 8
        (D) OTHER INFORMATION: /note="Xaa at position 8 is any
            hydrophobic amino acid."

(ix) FEATURE:
        (A) NAME/KEY: Modified-site
        (B) LOCATION: 12
        (D) OTHER INFORMATION: /note="Xaa at position 12 is Ala
            or Cys."

(ix) FEATURE:
        (A) NAME/KEY: Modified-site
        (B) LOCATION: 14
        (D) OTHER INFORMATION: /label=V- Y
            / note="Xaa at position 14 is any hydrophobic
            amino acid. Y=a fluorogenic donor or acceptor
            radical which follows Xaa at position 14. V=
            an aminoalkylcarboxylic acid which may or may
            not be inserted between Y and Xaa at position
            14."

(xi) SEQUENCE DESCRIPTION: SEQ ID NO:19:

```
Glu Arg Ala Gln Ala Gly Val Xaa Asn Ala Ser Xaa Arg Xaa
 1               5                  10
```

(2) INFORMATION FOR SEQ ID NO:20:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Z- W
            / note="Z=a fluorogenic donor or acceptor which
            precedes the amino acid at position 1. W=an
            aminoalkylcarboxylic acid which may or may not be
            inserted between Z and the amino acid at posiiton
            1."

(ix) FEATURE:
        (A) NAME/KEY: Modified-site
        (B) LOCATION: 7
        (D) OTHER INFORMATION: /note="Xaa at position 7 is any
            hydrophobic amino acid."

(ix) FEATURE:
        (A) NAME/KEY: Modified-site
        (B) LOCATION: 11
        (D) OTHER INFORMATION: /note="Xaa at position 11 is Ala
            or Cys."

(ix) FEATURE:
    (A) NAME/KEY: Modified-site
    (B) LOCATION: 13
    (D) OTHER INFORMATION: /note="Xaa at position 13 is any hydrophobic amino acid."

(ix) FEATURE:
    (A) NAME/KEY: Modified-site
    (B) LOCATION: 14
    (D) OTHER INFORMATION: /label=V-Y
        /note="Y=a fluorogenic donor or acceptor radical which follows the amino acid at position 14. V=an aminoalkylcarboxylic acid which may or may not be inserted between Y and the amino acid at position 14."

(xi) SEQUENCE DESCRIPTION: SEQ ID NO:20:

Arg Ala Gln Ala Gly Val Xaa Asn Ala Ser Xaa Arg Xaa Ala
1               5                   10

(2) INFORMATION FOR SEQ ID NO:21:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Z-W
            /note="Z=a fluorgenic donor or acceptor radical which precedes the amino acid at position 1. W=an aminoalkylcarboxylic acid which may or may not be inserted between Z and the amino acid at position 1."

(ix) FEATURE:
        (A) NAME/KEY: Modified-site
        (B) LOCATION: 6
        (D) OTHER INFORMATION: /note="Xaa at position 6 is any hydrophobic amino acid."

(ix) FEATURE:
        (A) NAME/KEY: Modified-site
        (B) LOCATION: 10
        (D) OTHER INFORMATION: /note="Xaa at position 10 is Ala or Cys."

(ix) FEATURE:
        (A) NAME/KEY: Modified-site
        (B) LOCATION: 12
        (D) OTHER INFORMATION: /note="Xaa at position 12 is any hydrophobic amino acid."

(ix) FEATURE:
        (A) NAME/KEY: Modified-site
        (B) LOCATION: 14
        (D) OTHER INFORMATION: /label=V-Y
            /note="Y=a fluorogenic donor or acceptor radical which follows the amino acid at position 14. V=an aminoalkylcarboxylic acid which may or may not be inserted between Y and the amino acid at position 14."

(xi) SEQUENCE DESCRIPTION: SEQ ID NO:21:

Ala Gln Ala Gly Val Xaa Asn Ala Ser Xaa Arg Xaa Ala Thr
1               5                   10

(2) INFORMATION FOR SEQ ID NO:22:

(i) SEQUENCE CHARACTERISTICS:
        (A) LENGTH: 14 amino acids
        (B) TYPE: amino acid (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=Z- W
        / note="Z=a fluorogenic donor or acceptor radical which precedes the amino acid at position 1. W=an aminoalkylcarboxylic acid which may or may not be inserted between Z and the amino acid at position 1."

(ix) FEATURE:
    (A) NAME/KEY: Modified-site
    (B) LOCATION: 5
    (D) OTHER INFORMATION: /note="Xaa at position 5 is any hydrophobic amino acid."

(ix) FEATURE:
    (A) NAME/KEY: Modified-site
    (B) LOCATION: 9
    (D) OTHER INFORMATION: /note="Xaa at position 9 is Ala or Cys."

(ix) FEATURE:
    (A) NAME/KEY: Modified-site
    (B) LOCATION: 11
    (D) OTHER INFORMATION: /note="Xaa at position 11 is any hydrophobic amino acid."

(ix) FEATURE:
    (A) NAME/KEY: Modified-site
    (B) LOCATION: 14
    (D) OTHER INFORMATION: /label=V- Y
        / note="Y=a fluorogenic donor or acceptor radical which follows the amio acid at position 14. V=an aminoalkylcarboxylic acid which may or may not be inserted between Y and the amino acid at position 14."

(xi) SEQUENCE DESCRIPTION: SEQ ID NO:22:

Gln Ala Gly Val Xaa Asn Ala Ser Xaa Arg Xaa Ala Thr Ala
1               5                   10

(2) INFORMATION FOR SEQ ID NO:23:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /label=Z- W
        / note="Z=a fluorogenic donor or acceptor radical which precedes the amino acid at position 1. W=an aminoalkylcarboxylic acid which may or may not be inserted between Z and the amino acid at position 1."

(ix) FEATURE:
    (A) NAME/KEY: Modified-site
    (B) LOCATION: 9
    (D) OTHER INFORMATION: /note="Xaa at position 9 is any hydrophobic amino acid."

(ix) FEATURE:
    (A) NAME/KEY: Modified-site
    (B) LOCATION: 13
    (D) OTHER INFORMATION: /note="Xaa at position 13 is Ala or Cys."

(ix) FEATURE:
    (A) NAME/KEY: Modified-site ( B ) LOCATION: 15
( D ) OTHER INFORMATION: /label=V- Y
/ note="Xaa at position 15 is any hydrophobic
amino acid. Y=a fluorogenic donor or acceptor
radical which follows Xaa at position 15. V=an
aminoalkylcarboxylic acid which may or may not
be inserted between Y and Xaa at position 15."

( x i ) SEQUENCE DESCRIPTION: SEQ ID NO:23:

| Ala | Glu | Arg | Ala | Gln | Ala | Gly | Val | Xaa | Asn | Ala | Ser | Xaa | Arg | Xaa |
|---|---|---|---|---|---|---|---|---|---|---|---|---|---|---|
| 1 | | | | 5 | | | | | 10 | | | | | 15 |

( 2 ) INFORMATION FOR SEQ ID NO:24:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=Z- W
/ note="Z=a fluorogenic donor or acceptor radical
which precedes the amino acid at position 1. W=an
aminoalkylcarboxylic acid which may or may not be
inserted between Z and the amino acid at position
1."

( i x ) FEATURE:
( A ) NAME/KEY: Modified-site
( B ) LOCATION: 8
( D ) OTHER INFORMATION: /note="Xaa at position 8 is any
hydrophobic amino acid."

( i x ) FEATURE:
( A ) NAME/KEY: Modified-site
( B ) LOCATION: 12
( D ) OTHER INFORMATION: /note="Xaa at position 12 is Ala
or Cys."

( i x ) FEATURE:
( A ) NAME/KEY: Modified-site
( B ) LOCATION: 14
( D ) OTHER INFORMATION: /note="Xaa at position 14 is any
hydrophobic amino acid."

( i x ) FEATURE:
( A ) NAME/KEY: Modified-site
( B ) LOCATION: 15
( D ) OTHER INFORMATION: /label=V- Y
/ note="Y=a fluorogenic donor or acceptor radical
which follows the amino acid at position 15. V=an
aminoalkylcarboxylic acid which may or may not
be inserted between Y and the amino acid at position
15."

( x i ) SEQUENCE DESCRIPTION: SEQ ID NO:24:

| Glu | Arg | Ala | Gln | Ala | Gly | Val | Xaa | Asn | Ala | Ser | Xaa | Arg | Xaa | Ala |
|---|---|---|---|---|---|---|---|---|---|---|---|---|---|---|
| 1 | | | | 5 | | | | | 10 | | | | | 15 |

( 2 ) INFORMATION FOR SEQ ID NO:25:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=Z- W / note="Z=a fluorogenic donor or acceptor radical
which precedes the amino acid at position 1. W=an
aminoalkylcarboxylic acid which may or may not be
inserted between Z and the amino acid at position 1."

( i x ) FEATURE:
    ( A ) NAME/KEY: Modified-site
    ( B ) LOCATION: 7
    ( D ) OTHER INFORMATION: /note="Xaa at position 7 is any
        hydrophobic amino acid."

( i x ) FEATURE:
    ( A ) NAME/KEY: Modified-site
    ( B ) LOCATION: 11
    ( D ) OTHER INFORMATION: /note="Xaa at position 11 is Ala
        or Cys."

( i x ) FEATURE:
    ( A ) NAME/KEY: Modified-site
    ( B ) LOCATION: 13
    ( D ) OTHER INFORMATION: /note="Xaa at position 13 is any
        hydrophobic amino acid."

( i x ) FEATURE:
    ( A ) NAME/KEY: Modified-site
    ( B ) LOCATION: 15
    ( D ) OTHER INFORMATION: /label=V- Y
        / note="Y=a fluorogenic donor or acceptor radical
        which follows the amino acid at position 15. V=an
        aminoalkylcarboxylic acid which may or may not be
        inserted between Y and the amino acid at position
        15."

( x i ) SEQUENCE DESCRIPTION: SEQ ID NO:25:

Arg Ala Gln Ala Gly Val Xaa Asn Ala Ser Xaa Arg Xaa Ala Thr
1               5                   10                  15

( 2 ) INFORMATION FOR SEQ ID NO:26:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Z- W
        / note="Z=a fluorogenic donor or acceptor radical
        which precedes the amino acid at position 1. W=an
        aminoalkylcarboxylic acid which may or may not be
        inserted between Z and the amino acid at position
        1."

( i x ) FEATURE:
    ( A ) NAME/KEY: Modified-site
    ( B ) LOCATION: 6
    ( D ) OTHER INFORMATION: /note="Xaa at position 6 is any
        hydrophobic amino acid."

( i x ) FEATURE:
    ( A ) NAME/KEY: Modified-site
    ( B ) LOCATION: 10
    ( D ) OTHER INFORMATION: /note="Xaa at position 10 is Ala
        or Cys."

( i x ) FEATURE:
    ( A ) NAME/KEY: Modified-site
    ( B ) LOCATION: 12
    ( D ) OTHER INFORMATION: /note="Xaa at position 12 is any
        hydrophobic amino acid."

( i x ) FEATURE:
    ( A ) NAME/KEY: Modified-site
    ( B ) LOCATION: 15
    ( D ) OTHER INFORMATION: /label=V- Y / note="Y=a fluorogenic donor or acceptor radical
which follows the amino acid at position 15. V=an
aminoalkylcarboxylic acid which may or may not be
inserted between Y and the amino acid at position
15."

( x i ) SEQUENCE DESCRIPTION: SEQ ID NO:26:

Ala Gln Ala Gly Val Xaa Asn Ala Ser Xaa Arg Xaa Ala Thr Ala
1               5                       10                      15

( 2 ) INFORMATION FOR SEQ ID NO:27:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Z- W
            / note="Z=a fluorogenic donor or acceptor radical
            which precedes the amino acid at position 1. W=an
            aminoalkylcarboxylic acid which may or may not be
            inserted between Z and the amino acid at position
            1."

( i x ) FEATURE:
        ( A ) NAME/KEY: Modified-site
        ( B ) LOCATION: 10
        ( D ) OTHER INFORMATION: /note="Xaa at position 10 is any
            hydrophobic amino acid."

( i x ) FEATURE:
        ( A ) NAME/KEY: Modified-site
        ( B ) LOCATION: 14
        ( D ) OTHER INFORMATION: /note="Xaa at position 14 is Ala
            or Cys."

( i x ) FEATURE:
        ( A ) NAME/KEY: Modified-site
        ( B ) LOCATION: 16
        ( D ) OTHER INFORMATION: /label=V- Y
            / note="Xaa at position 16 is any hydrophobic
            amino acid. Y=a fluorogenic donor or acceptor
            radical which follows Xaa at position 16. V=
            an aminoalkylcarboxylic acid which may or may
            not be inserted Y and Xaa at position 16."

( x i ) SEQUENCE DESCRIPTION: SEQ ID NO:27:

Val Ala Glu Arg Ala Gln Ala Gly Val Xaa Asn Ala Ser Xaa Arg Xaa
1               5                       10                      15

( 2 ) INFORMATION FOR SEQ ID NO:28:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Z- W
            / note="Z=a fluorogenic donor or acceptor radical
            which precedes the amino acid at position 1. W=an
            aminoalkylcarboxylic acid which may or may not be
            inserted between Z and the amino acid at position
            1."

( i x ) FEATURE:
        ( A ) NAME/KEY: Modified-site (B) LOCATION: 9
(D) OTHER INFORMATION: /note="Xaa at position 9 is any
hydrophobic amino acid."

(ix) FEATURE:
(A) NAME/KEY: Modified-site
(B) LOCATION: 13
(D) OTHER INFORMATION: /note="Xaa at position 13 is Ala
or Cys."

(ix) FEATURE:
(A) NAME/KEY: Modified-site
(B) LOCATION: 15
(D) OTHER INFORMATION: /note="Xaa at position 15 is any
hydrophobic amino acid."

(ix) FEATURE:
(A) NAME/KEY: Modified-site
(B) LOCATION: 16
(D) OTHER INFORMATION: /label=V- Y
/ note="Y=a fluorogenic donor or acceptor radical
which follows the amino acid at position 16. V=an
aminoalkylcarboxylic acid which may or may not be
inserted between Y and the amino acid at position
16."

(xi) SEQUENCE DESCRIPTION: SEQ ID NO:28:

Ala Glu Arg Ala Gln Ala Gly Val Xaa Asn Ala Ser Xaa Arg Xaa Ala
1               5                   10                  15

(2) INFORMATION FOR SEQ ID NO:29:

(i) SEQUENCE CHARACTERISTICS:
(A) LENGTH: 16 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Z- W
/ note="Z=a fluorogenic donor or acceptor radical
which precedes the amino acid at position 1. W=an
aminoalkylcarboxylic acid which may or may not be
inserted between Z and the amino acid at position
1."

(ix) FEATURE:
(A) NAME/KEY: Modified-site
(B) LOCATION: 8
(D) OTHER INFORMATION: /note="Xaa at position 8 is any
hydrophobic amino acid."

(ix) FEATURE:
(A) NAME/KEY: Modified-site
(B) LOCATION: 12
(D) OTHER INFORMATION: /note="Xaa at position 12 is Ala
or Cys."

(ix) FEATURE:
(A) NAME/KEY: Modified-site
(B) LOCATION: 14
(D) OTHER INFORMATION: /note="Xaa at position 14 is any
hydrophobic amino acid."

(ix) FEATURE:
(A) NAME/KEY: Modified-site
(B) LOCATION: 16
(D) OTHER INFORMATION: /label=V- Y
/ note="Y=a fluorogenic donor or acceptor radical
which follows the amino acid at position 16. V=an
aminoalkylcarboxylic acid which may or may not be
inserted between Y and the amino acid at position
16."

(xi) SEQUENCE DESCRIPTION: SEQ ID NO:29:

5,506,115

47                                                                           48
-continued

```
Glu Arg Ala Gln Ala Gly Val Xaa Asn Ala Ser Xaa Arg Xaa Ala Thr
1               5                   10                  15
```

( 2 ) INFORMATION FOR SEQ ID NO:30:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=Z- W
      / note="Z=a fluorogenic donor or acceptor radical
      which precedes the amino acid at position 1. W=an
      aminoalkylcarboxylic acid which may or may not be
      inserted between Z and the amino acid at position
      1."

( i x ) FEATURE:
    ( A ) NAME/KEY: Modified-site
    ( B ) LOCATION: 7
    ( D ) OTHER INFORMATION: /note="Xaa at position 7 is any
      hydrophobic amino acid."

( i x ) FEATURE:
    ( A ) NAME/KEY: Modified-site
    ( B ) LOCATION: 11
    ( D ) OTHER INFORMATION: /note="Xaa at position 11 is Ala
      or Cys."

( i x ) FEATURE:
    ( A ) NAME/KEY: Modified-site
    ( B ) LOCATION: 13
    ( D ) OTHER INFORMATION: /note="Xaa at position 13 is any
      hydrophobic amino acid."

( i x ) FEATURE:
    ( A ) NAME/KEY: Modified-site
    ( B ) LOCATION: 16
    ( D ) OTHER INFORMATION: /label=V- Y
      / note="Y=a fluorogenic donor or acceptor radical
      which follows the amino acid at position 16. V=an
      aminoalkylcarboxylic which may or may not be
      inserted between Y and the amino acid at position
      16."

( x i ) SEQUENCE DESCRIPTION: SEQ ID NO:30:

```
Arg Ala Gln Ala Gly Val Xaa Asn Ala Ser Xaa Arg Xaa Ala Thr Ala
1               5                   10                  15
```

( 2 ) INFORMATION FOR SEQ ID NO:31:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=Z
      / note="Xaa at position 1 is Gly or 4Abu or Acp or
      5- aminopentanoic acid or 7-aminoheptanoic acid.
      Z=a fluorogenic donor or acceptor radical
      which precedes Xaa at position 1."

( i x ) FEATURE:
    ( A ) NAME/KEY: Modified-site
    ( B ) LOCATION: 4
    ( D ) OTHER INFORMATION: /note="Xaa at position 4 is any hydrophobic amino acid."

(ix) FEATURE:
(A) NAME/KEY: Modified-site
(B) LOCATION: 8
(D) OTHER INFORMATION: /note="Xaa at position 8 is Ala or Cys."

(ix) FEATURE:
(A) NAME/KEY: Modified-site
(B) LOCATION: 10
(D) OTHER INFORMATION: /note="Xaa at position 10 is any hydrophobic amino acid."

(ix) FEATURE:
(A) NAME/KEY: Modified-site
(B) LOCATION: 11
(D) OTHER INFORMATION: /label=Y
/note="Y=a fluorogenic donor or acceptor radical which follows the amino acid at position 11."

(xi) SEQUENCE DESCRIPTION: SEQ ID NO:31:

Xaa Gly Val Xaa Asn Ala Ser Xaa Arg Xaa Ala
1               5                   10

(2) INFORMATION FOR SEQ ID NO:32:

(i) SEQUENCE CHARACTERISTICS:
(A) LENGTH: 11 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Z
/note="Xaa at position 1 is 4Abu. Z=4-(4'- dimethlylaminophenylazo)benzoyl (DABCYL) which precedes Xaa at position 1."

(ix) FEATURE:
(A) NAME/KEY: Modified-site
(B) LOCATION: 11
(D) OTHER INFORMATION: /label=Y
/note=" Y=5-[(2-aminoethyl)amino]naphthalene-1-sulfonic acid (EDANS) which follows the amino acid at position 11."

(xi) SEQUENCE DESCRIPTION: SEQ ID NO:32:

Xaa Gly Val Val Asn Ala Ser Ala Arg Leu Ala
1               5                   10

(2) INFORMATION FOR SEQ ID NO:33:

(i) SEQUENCE CHARACTERISTICS:
(A) LENGTH: 9 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Z
/note="Xaa at position 1 is Gly or 4Abu or Acp or 5- aminopentanoic acid or 7-aminoheptanoic acid. Z=a fluorogenic donor or acceptor radical which precedes Xaa at position 1."

(ix) FEATURE:
(A) NAME/KEY: Modified-site
(B) LOCATION: 3

(D) OTHER INFORMATION: /note="Xaa at position 3 is any
hydrophobic amino acid."

(ix) FEATURE:
(A) NAME/KEY: Modified-site
(B) LOCATION: 7
(D) OTHER INFORMATION: /note="Xaa at position 7 is Ala or
Cys."

(ix) FEATURE:
(A) NAME/KEY: Modified-site
(B) LOCATION: 9
(D) OTHER INFORMATION: /label=Y
/ note="Xaa at position 9 is any hydrophobic amino
acid. Y=a fluorogenic donor or acceptor radical
which follows Xaa at position 9."

(xi) SEQUENCE DESCRIPTION: SEQ ID NO:33:

Xaa Val Xaa Asn Ala Ser Xaa Arg Xaa
1               5

(2) INFORMATION FOR SEQ ID NO:34:

(i) SEQUENCE CHARACTERISTICS:
(A) LENGTH: 9 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Z
/ note="Xaa at position 1 is 4Abu.
Z=4-(4'- dimethylaminophenylazo)benzoyl
(DABCYL), which precedes Xaa at position 1."

(ix) FEATURE:
(A) NAME/KEY: Modified-site
(B) LOCATION: 9
(D) OTHER INFORMATION: /label=Y
/ note="Y=5-[(2-aminoethyl)amino]naphthalene-1-sulfonic
acid which follows amino acid at position 9."

(xi) SEQUENCE DESCRIPTION: SEQ ID NO:34:

Xaa Val Val Asn Ala Ser Ala Arg Leu
1               5

(2) INFORMATION FOR SEQ ID NO:35:

(i) SEQUENCE CHARACTERISTICS:
(A) LENGTH: 19 amino acids
(B) TYPE: amino acid
(D) TOPOLOGY: linear (ii) MOLECULE TYPE: peptide (xi) SEQUENCE DESCRIPTION: SEQ ID NO:35:

Val Ala Glu Arg Ala Gln Ala Gly Val Val Asn Ala Ser Cys Arg Leu
1               5                   10                  15

Ala Thr Ala (2) INFORMATION FOR SEQ ID NO:36:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:

( A ) NAME/KEY: Modified-site
( B ) LOCATION: 4
( D ) OTHER INFORMATION: /label=Y
/ note="Y=5-[(2-aminoethyl)amino]naphthalene-1-sulfonic acid which follows amino acid at position 4."

( x i ) SEQUENCE DESCRIPTION: SEQ ID NO:36:

Ser Ala Arg Leu
1

What is claimed is:

1. A compound consisting of Formula II

Z-W-Gly-Val-Val-Asn-Ala-Ser-Ala-Arg-Leu-Ala-Y    (II)

[SEQ ID NO:31]

wherein W is an aminoalkylcarboxylic acid;

wherein one of Y and z is a fluorogenic radical and the other is an acceptor radical.

2. Compound of claim 1 wherein W is a lower aminoalkylcarboxylic acid; wherein Y is a fluorogenic radical; and wherein z is an acceptor radical.

3. Compound of claim 2 wherein W is independently selected from glycine, 4-aminobutyric acid, 5-aminopentanoic acid, 6-aminocaproic acid and 7-aminoheptanoic acid; wherein Y is selected from EDANS, Abz, DANSYL, nicotinic acid, 4-guanidino-benzoic acid, N-methyl-Abz, 4-chloro-Abz, 5-chloro-Abz, 6-chloro-Abz, 3,5-dibromo-Abz, 6-amino-nicotinic acid, 2-amino-nicotinic acid, 2-chloronicotinic acid, niflumic acid and fluorogenic derivatives thereof; and wherein Z is selected from tryptophan, tyrosine, phenylalanine, p-nitrophenylalanine, m-nitrophenylalanine, DABSYL, DABCYL and halogenated derivatives thereof.

4. Compound of claim 3 which is DABCYL-γ-Abu-Gly-Val-Val-Asn-Ala-Ser-Ala-Arg-Leu-Ala-EDANS [SEQ ID NO:32].

5. A compound consisting of Formula III

Z—W—Val—Val—Asn—Ala—Ser—Ala—Arg—Leu—Y    (III)

[SEQ ID NO: 33]

wherein W is an aminoalkylcarboxylic acid; wherein one of Y and Z is a fluorogenic radical and the other is an acceptor radical.

6. Compound of claim 5 wherein W is lower aminoalkylcarboxylic acid; wherein Y is a fluorogenic radical; and wherein z is an acceptor radical.

7. Compound of claim 6 wherein W is selected from glycine, 4-aminobutyric acid, 5-aminopentanoic acid, 6-aminocaproic acid and 7-aminoheptanoic acid; wherein Y is selected from EDANS, Abz, DANSYL, nicotinic acid, 4-guanidinobenzoic acid, N-methyl-Abz, 4-chloro-Abz, 5-chloro-Abz, 6-chloro-Abz, 3,5-dibromo-Abz, 6-aminonicotinic acid, 2-amino-nicotinic acid, 2-chloronicotinic acid, niflumic acid and fluorogenic derivatives thereof; and wherein Z is selected from tryptophan, tyrosine, phenylalanine, p-nitrophenylalanine, m-nitrophenylalanine, DABSYL, DABCYL and halogenated derivatives thereof.

8. Compound of claim 7 which is DABCYL-γ-Abu-Val-Val-Asn-Ala-Ser-Ala-Arg-Leu-EDANS [SEQ ID NO:34].

9. A method of using compounds of claim 1 as a substrate for a herpesvirus protease, said method comprising:

adding said compounds to a solution containing said herpesvirus protease; and monitoring an increase in fluorescence as a function of time.

10. A method of using compounds of claim 1 in an assay to identify an inhibitor of a herpesvirus protease, said method comprising:

adding said compounds to a solution containing the herpesvirus protease and the inhibitor;

monitoring an increase in fluorescence as a function of time; and calculating the amount of protease inhibition.

11. A method of using compounds of claim 5 in an assay to identify an inhibitor of a herpesvirus protease, said method comprising adding said compounds to a solution containing the herpesvirus protease and the inhibitor; monitoring an increase in fluorescence as a function of time; and calculating the amount of protease inhibition.

* * * * *